(12) United States Patent
Kishi (10) Patent No.: US 11,754,555 B2
(45) Date of Patent: *Sep. 12, 2023

(54) PAD FOR IMMUNOCHROMATOGRAPHIC DEVICE AND IMMUNOCHROMATOGRAPHIC DEVICE, IMMUNOCHROMATOGRAPHIC KIT AND IMMUNOCHROMATOGRAPHIC DETECTION METHOD USING PAD

(71) Applicant: TANAKA KIKINZOKU KOGYO K.K., Tokyo (JP)

(72) Inventor: Hiroshi Kishi, Kanagawa (JP)

(73) Assignee: TANAKA KIKINZOKU KOGYO K.K., Tokyo (JP)

( * ) Notice: Subject to any disclaimer, the term of this patent is extended or adjusted under 35 U.S.C. 154(b) by 359 days.

This patent is subject to a terminal disclaimer.

(21) Appl. No.: 16/440,880

(22) Filed: Jun. 13, 2019

(65) Prior Publication Data

US 2019/0383802 A1    Dec. 19, 2019

(30) Foreign Application Priority Data

Jun. 14, 2018 (JP) ............................. JP2018-114009

(51) Int. Cl.
  *G01N 33/53*     (2006.01)
  *G01N 33/543*    (2006.01)
  (Continued)

(52) U.S. Cl.
  CPC ..... *G01N 33/5306* (2013.01); *G01N 33/5308* (2013.01); *G01N 33/538* (2013.01);
  (Continued)

(58) Field of Classification Search
  CPC ......... G01N 33/5306; G01N 33/54393; G01N 33/558; G01N 33/54326; G01N 33/5375;
  (Continued)

(56) References Cited

U.S. PATENT DOCUMENTS 6,119,701 A *  9/2000  Cerami .................... A24D 3/10
                                                            131/331
2003/0180446 A1*  9/2003  Totokawa .............. G01N 27/12
                                                            427/58
(Continued)

FOREIGN PATENT DOCUMENTS

EP    3 425 398 A1    1/2019
JP    2012-189346 A   10/2012
(Continued)

*Primary Examiner* — Matthew D Krcha
*Assistant Examiner* — Sophia Y Lyle
(74) *Attorney, Agent, or Firm* — Foley & Lardner LLP (57) ABSTRACT

According to a pad which is used for an immunochromatographic device for extracting a substance to be detected contained in a detection target in an analyte with nitrous acid and which contains an acid anhydride having vapor pressure at 25° C. of $5\times10^{-2}$ Pa or less and solubility in water at 25° C. of 0.1 mg/L or more, the storage stability is improved; a substance to be detected contained in an analyte is detected with high sensitivity; and the complexity of production is reduced.

14 Claims, 3 Drawing Sheets

(51) Int. Cl.
*G01N 33/537* (2006.01)
*G01N 33/538* (2006.01)
(52) U.S. Cl.
CPC ... *G01N 33/5375* (2013.01); *G01N 33/54326* (2013.01); *G01N 33/54388* (2021.08); *G01N 33/54393* (2013.01)
(58) Field of Classification Search
CPC .. G01N 33/538; G01N 33/5308; G01N 1/405; C07D 499/30; D06P 1/65143
See application file for complete search history.

(56) References Cited

U.S. PATENT DOCUMENTS

| | | | | |
|---|---|---|---|---|
| 2008/0206849 A1* | 8/2008 | Zak | ............... | G01N 33/558 |
| | | | | 435/287.2 |
| 2013/0105316 A1* | 5/2013 | Nakayama | ........... | G01N 27/447 |
| | | | | 549/252 |
| 2013/0233381 A1* | 9/2013 | Win | ............... | C08G 73/105 |
| | | | | 524/588 |
| 2016/0370368 A1* | 12/2016 | Kato | ............ | G01N 33/5306 |

FOREIGN PATENT DOCUMENTS

| | | | |
|---|---|---|---|
| JP | 2014-232064 A | 12/2014 | |
| JP | 2015-034719 A | 2/2015 | |
| WO | WO-2015013456 A1 * | 1/2015 | ............. A61L 27/50 |
| WO | WO-2017/150733 A1 | 9/2017 | |

\* cited by examiner

PAD FOR IMMUNOCHROMATOGRAPHIC DEVICE AND IMMUNOCHROMATOGRAPHIC DEVICE, IMMUNOCHROMATOGRAPHIC KIT AND IMMUNOCHROMATOGRAPHIC DETECTION METHOD USING PAD

TECHNICAL FIELD

The present invention relates to a pad for an immunochromatographic device and to an immunochromatographic device, an immunochromatographic kit and an immunochromatographic detection method using the pad.

BACKGROUND ART

Recently, an immunoassay of the strip type for immunochromatography has an increasing versatility as a simple extracorporeal diagnostic kit or a mobile diagnostic device for detecting a detection target in an analyte using a specific reactivity of an antibody.

In particular, there is now enhanced interest in simple test devices for testing the presence or absence of infection with a pathogen such as influenza viruses and bacteria based on an immunochromatographic method, and the test devices have been studied and developed.

For example, diagnosis of infection by *Streptococcus pyogenes* (to be also referred to as hemolytic streptococci) is made through a test using a group-specific polysaccharide as an antigen. Although methods using an enzyme, a bacteriophage, hydrochloric acid, hypochlorous acid and the like are known as methods for extracting the polysaccharide, an extraction method using nitrous acid is the most common method.

Advantages of the extraction method using nitrous acid are that the extraction efficiency of the polysaccharide is high and that nitrous acid is inexpensive and easy to handle. However, one of its disadvantages is that nitrous acid has to be prepared each time by mixing a nitrous acid compound such as sodium nitrite and an organic acid before the extraction since nitrous acid itself is an unstable compound which is easily decomposed. Examples of the organic acid include acetic acid, citric acid, tartaric acid, itaconic acid, oxalic acid, succinic acid, glycolic acid, benzoic acid, benzenesulfonic acid and the like (for example, see Patent Literatures 1 and 2 below).

In the conventional test device containing an organic acid and a nitrous acid compound, the organic acid and the nitrous acid compound may partially diffuse in the test device, thus come into contact with each other and generate nitrous acid during the storage of the test device. When the generation of nitrous acid progresses during the storage of the test device, nitrous acid is not generated sufficiently at the actual use of the test device, and the extraction efficiency of the detection target and the detection sensitivity decrease. Thus, there is room for improvement in the storage stability of the test device in this regard.

In order to solve the problem, Patent Literature 3 below proposes an immunochromatographic device for detecting a detection target in an analyte which includes a sample droplet receiving member, a labeling substance retaining member having a labeling substance containing part, a chromatography medium member having a detection part and an absorption member and which contains a nitrous acid compound and an organic acid or an organic acid derivative. In the immunochromatographic device, the sample droplet receiving member, the labeling substance retaining member, the chromatography medium member and the absorption member are arranged in a manner that a sample develops in this order. The immunochromatographic device has a part containing the nitrous acid compound and a part containing the organic acid or the organic acid derivative at upstream positions from the labeling substance containing part, and the part containing the nitrous acid compound and the part containing the organic acid or the organic acid derivative are not substantially in contact with each other in the thickness direction.

[Patent Literature 1] JP-A-2014-232064
[Patent Literature 2] JP-A-2015-34719
[Patent Literature 3] WO2017/150733

SUMMARY OF INVENTION

However, according to the investigation of the present inventors, although the immunochromatographic device described in Patent Literature 3 has a certain effect on the storage stability, problems such as decomposition, volatilization and sublimation of the acid in the device arise depending on the kind of the acid used, and the acid sometimes reacts with the nitrous acid compound during the storage. Therefore, there is room for improvement in the storage stability. Moreover, a special structure in which the part containing the nitrous acid compound and the part containing the organic acid or the organic acid derivative are not substantially in contact with each other in the thickness direction is required, and the production is complicated. Furthermore, there is room for improvement also in the detection sensitivity.

Therefore, an object of the invention is to provide a pad used for an immunochromatographic device which can further improve the storage stability, detect a substance to be detected contained in an analyte with high sensitivity and reduce the complexity of production and to provide an immunochromatographic device, an immunochromatographic kit and an immunochromatographic detection method using the pad.

As a result of intensive investigation, the present inventors have found that the problems can be solved using an acid anhydride having specific vapor pressure and specific solubility instead of the organic acids used for the conventional immunochromatographic devices and thus have completed the invention.

That is, the invention is as follows.

1. A pad used for an immunochromatographic device for extracting a substance to be detected contained in a detection target in an analyte with nitrous acid, containing:
an acid anhydride having vapor pressure at 25° C. of $5 \times 10^{-2}$ Pa or less and solubility in water at 25° C. of 0.1 mg/L, or more.

2. The pad according to the above 1, wherein the vapor pressure at 25° C. of the acid anhydride is $2 \times 10^{-2}$ Pa or less.

3. The pad according to the above 1 or 2, wherein the acid anhydride is one or more kinds selected from a group consisting of bicyclo[2,2,2]oct-7-ene-2,3,5,6-tetracarboxylic dianhydride, pyromellitic anhydride, 1,2,4,5-cyclohexanetetracarboxylic dianhydride, 4-(2,5-dioxotetrahydrofuran-3-yl)-1,2,3,4-tetrahydronaphthalene-1,2-dicarboxylic anhydride, 3-acetamidophthalic anhydride, and 4-(1-propynyl)phthalic anhydride.

4. The pad according to any one of the above 1 to 3, wherein a content of the acid anhydride in the pad is 0.4 μmol to 8.4 μmol, per one pad.

5. An immunochromatographic device for extracting a substance to be detected contained in a detection target in an analyte with nitrous acid, containing the pad according to any one of the above 1 to 4.

6. The immunochromatographic device for detecting a substance to be detected contained in a detection target in an analyte according to the above 5, containing:
a sample droplet receiving member;
a labeling substance retaining member having a labeling substance containing part;
a chromatography medium member having a detection part;
an absorption member;
a nitrous acid compound; and
an acid anhydride having vapor pressure at 25° C. of $5 \times 10^{-2}$ Pa or less and solubility in water at 25° C. of 0.1 mg/L or more,
wherein the sample droplet receiving member, the labeling substance retaining member, the chromatography medium member and the absorption member are arranged in a manner that a sample develops in the members in this order,
the immunochromatographic device has a part containing the nitrous acid compound and a part containing the acid anhydride at upstream positions from the detection part, and the part containing the acid anhydride is composed of the pad according to any one of the above 1 to 4.

7. The immunochromatographic device according to the above 6, wherein the nitrous acid compound is a nitrite.

8. An immunochromatographic kit, containing:
the immunochromatographic device according to any one of the above 5 to 7; and
an analyte dilution solution for diluting and developing the analyte.

9. An immunochromatographic detection method for detecting a substance to be detected contained in a detection target in an analyte using the immunochromatographic kit according to the above 8, containing the following (i) to (v):
(i) dropping an solution containing the analyte obtained by diluting the analyte with the analyte dilution solution to the sample droplet receiving member;
(ii) extracting the substance to be detected from the analyte with nitrous acid generated through reaction of the nitrous acid compound and the acid anhydride having vapor pressure at 25° C. of $5 \times 10^{-2}$ Pa or less and solubility in water at 25° C. of 0.1 mg/L or more;
(iii) labeling the substance to be detected in the labeling substance retaining member;
(iv) allowing the solution containing the analyte to move on the chromatography medium member and detecting the substance to be detected in the detection part; and
(v) absorbing the solution containing the analyte with the absorption member.

Since the pad of the invention is characterized by containing an acid anhydride having vapor pressure at 25° C. of $5 \times 10^{-2}$ Pa or less, the sublimation of the acid anhydride from the pad is inhibited. Therefore, when the pad in the invention is applied to an immunochromatographic device wherein nitrous acid is generated, a storage stability improves since sublimation of the acid anhydride in the device is inhibited during storage thereof and generation of nitrous acid by reaction of the acid anhydride with nitrite can be inhibited. Additionally, as a result of inhibiting sublimation of the acid anhydride from the pad, generation efficiency of nitrous acid in case of carrying out test with application to the above device is increased, by which a detection target can be detected with high sensitivity.

Moreover, since an acid anhydride having solubility in water at 25° C. of 0.1 mg/L or more is used, the generation efficiency of nitrous acid of the device improves, and the substance to be detected can be detected with high sensitivity.

The storage stability and the detection sensitivity of the immunochromatographic device and the immunochromatographic kit of the invention are improved, and the complexity of their production can be avoided since a special structure in which the part containing the nitrous acid compound and the part containing the organic acid or the organic acid derivative are not substantially in contact with each other in the thickness direction is not required.

Since an acid anhydride having vapor pressure at 25° C. of $5 \times 10^{-2}$ Pa or less is used in the immunochromatographic detection method of the invention, the sublimation of the acid anhydride in the immunochromatographic device is prevented. As a result, the generation of nitrous acid is also inhibited, and the storage stability improves. Moreover, since an acid anhydride having solubility in water at 25° C. of 0.1 mg/L or more is used, the generation efficiency of nitrous acid during the use of the device improves, and the substance to be detected can be detected with high sensitivity.

DESCRIPTION OF EMBODIMENTS

Embodiments of the invention are explained in detail below.

An embodiment of the invention is based on a pad used for an immunochromatographic device for detecting a detection target with detection means by extracting a substance to be detected (an antigen) from the detection target in an analyte and developing a complex formed through reaction with a binding substance (an antibody) that specifically binds to the substance to be detected (the antigen) (antigen-antibody reaction) on a chromatography medium and based on an immunochromatographic device, an immunochromatographic kit and an immunochromatographic detection method which use the pad (sometimes simply called as an "immunochromatographic detection system" below).

As the antibody which most specifically reacts with and binds to the antigen, for example, a monoclonal antibody, a polyclonal antibody or another known antibody which specifically binds to the antigen can be used.

By labeling the antibody, the detection target can be detected. As the label, an enzyme, a coloring substance, a fluorescent substance, a radioactive substance or the like can be used. For example, the label may be selected in a manner that the characteristics of the immunochromatographic detection method, namely the simple operation and the short test period, are exhibited, or the label may be selected taking the types of the antibody, the antigen and the like into consideration.

In order that the characteristics of the immunochromatographic detection method, namely the simple operation and the relatively short determination period, can be exhibited, the detection means is characterized by having the property of enabling accurate determination by a visual evaluation. When the accuracy and the like are important, however, various types of detection means such as spectrophotometric detection and radiation detection can be additionally used for the detection.

Any bacterium can be applied as the detection target in the invention as long as a bacterium-specific antigen is extracted from the bacterium with nitrous acid generated by the immunochromatographic detection system of the invention. In particular, a detection target containing a Gram-positive bacterium having a thick peptidoglycan layer is preferably used.

Examples include staphylococci, streptococci, pneumococci, bacilli, Bacillus anthracis, Bacillus cereus, Corynebacterium diphtherias, Listeria, Clostridium tetani, Clostridium botulinum, Clostridium perfringens and the like. The invention is preferably used for staphylococci, streptococci and pneumococci, which are cocci, among these examples. The invention is most preferably used for streptococci, particularly hemolytic streptococci.

The analyte containing the detection target can be, for example, not only a biological sample such as saliva, nasal discharge, nasal swab, nasal aspirate, sputum, pharyngeal swab, alveolar lavage fluid, rectal swab, fecal suspension, urine and amniotic fluid but also a sample such as food extract, service water, sewage and culture solution, and the analyte is not particularly limited.

In particular, the invention is useful when the causative bacteria contained in such an analyte include a Gram-positive bacterium, especially a hemolytic *streptococcus*. In the invention, the detection target can be a hemolytic *streptococcus* contained in saliva or the like collected from a patient with a respiratory disease or the like, and the detection target, the hemolytic *streptococcus*, can be detected by detecting a polysaccharide extracted from the hemolytic *streptococcus* as a substance to be detected.

Although embodiments of the immunochromatographic detection system of the invention are explained one by one below, the invention is not limited to the embodiments shown below.

The pad of the invention is characterized by being used for an immunochromatographic device for extracting a substance to be detected contained in a detection target with nitrous acid and by containing an acid anhydride having vapor pressure at 25° C. of $5\times10^{-2}$ Pa or less and solubility in water at 25° C. of 0.1 mg/L or more (sometimes simply called as "the acid anhydride" below).

The pad in the invention is used as a member through which a liquid sample passes (develops) of the members used for the immunochromatographic device. The material, the form and the like of the pad are not particularly limited as long as the pad absorbs a liquid sample and as long as a liquid and the detection target can pass through the pad. In particular, a porous member is preferably used, and examples include cellulose filter paper, recycled cellulose filter paper, glass fiber filter paper, polyurethane, polyacetate, cellulose acetate, nylon, cotton cloth and the like. Regarding the shapes of the members, for example, sheets can be used.

The vapor pressure at 25° C. of the acid anhydride is $5\times10^{-2}$ Pa or less; preferably $2\times10^{-2}$ Pa or less; further preferably $1\times10^{-2}$ Pa or less; and particularly preferably $5\times10^{-3}$ Pa or less.

By adjusting the vapor pressure as described above, sublimation of the acid anhydride from the pad is inhibited and generation efficiency of nitrous acid improves at using the pad, by which a substance to be detected can be detected with high sensitivity.

A value of a known database (calculated value) can be used as the vapor pressure. The increase or the decrease in the weight of the acid anhydride after subjecting the acid anhydride to reduced pressure of 20 Pa at 25° C. for 12 hours is preferably within 5%.

The solubility in water at 25° C. of the acid anhydride used in the invention is 0.1 mg/L or more; preferably 1 mg/L or more; and more preferably 10 mg/L or more.

By setting the solubility in the above manner, the acid anhydride can rapidly dissolve in the solution containing analyte. Therefore, the generation efficiency of nitrous acid improves, and the detection sensitivity of the substance to be detected can be further improved.

A value of a database (calculated value) can be used as the solubility.

The acid anhydride used in the invention is preferably a compound which has two or more acid anhydride groups in one molecule. The vapor pressure of the acid anhydride relates to its molecular weight, and the vapor pressure tends to decrease as the molecular weight becomes higher. When the molecular weight is high, however, the solubility of the acid anhydride in water tends to decrease due to the influence of the hydrophobic carbon chain or the like. On the other hand, the amount of the acid anhydride per unit weight of a compound having two or more acid anhydride groups in one molecule is relatively high, and the compound is highly hydrophilic. Thus, such a compound can maintain excellent storage stability and can further improve the detection sensitivity. When the amount of the acid anhydride per unit weight is too high, however, the pH of the solution containing analyte decreases, and a problem of inhibition of the antigen-antibody reaction may arise. Therefore, the number of the acid anhydride groups contained in one molecule is preferably three or less. A compound having two acid anhydride groups in one molecule (an acid dianhydride) is most preferable.

In this connection, it is preferable that examples of an acid anhydride used in the invention do not include an acid anhydride having two or more benzene rings for high solubility and detection of a detection target with high sensitivity.

Specific examples of the acid anhydride used in the invention include tetracarboxylic dianhydrides such as bicyclo[2,2,2]oct-7-ene-2,3,5,6-tetracarboxylic dianhydride, pyromellitic anhydride and 1,2,4,5-cyclohexanetetracarboxylic dianhydride, 4,4'-biphthalic anhydride, 4-(2,5-dioxotetrahydrofuran-3-yl)-1,2,3,4-tetrahydronaphthalene-1,2-dicarboxylic anhydride, 3-acetamidophthalic anhydride, 4-(1-propynyl)phthalic anhydride, 2,3-naphthalenedicarboxylic anhydride, 1,2-naphthalenedicarboxylic anhydride and the like, and a kind thereof or a combination of two or more kinds thereof may be used. Particularly, compounds having two or more acid anhydride groups per one molecule such as bicyclo[2,2,2]oct-7-ene-2,3,5,6-tetracarboxylic dianhydride, pyromellitic anhydride, 1,2,4,5-cyclohexanetetracarboxylic dianhydride, and 4-(2,5-dioxotetrahydrofuran-3-yl)-1,2,3,4-tetrahydronaphthalene-1,2-dicarboxylic anhydride are preferable.

A content of the acid anhydride in the pad of the invention is, per one pad, preferably from 0.4 µmol to 8.4 µmol; further preferably from 0.6 µmol to 4.0 µmol; and particularly preferably from 0.8 µmol to 2.0 µmol. Additionally, a content of the acid anhydride in unit area of the pad is preferably 0.4 µmol/cm$^2$ to 8.4 µmol/cm$^2$; further preferably from 0.6 µmol/cm$^2$ to 4.0 µmol/cm$^2$; and particularly preferably from 0.8 µmol/cm$^2$ to 2.0 µmol/cm$^2$. With such a content, the extraction efficiency of the substance to be detected improves, and as a result, the detection sensitivity of the substance to be detected can be further improved.

Since an acid anhydride having specific vapor pressure is used for the pad of the invention, the sublimation of the acid, which occurs in the conventional techniques, does not occur easily, and the reaction with the nitrous acid compound during the storage can be inhibited. Therefore, the storage stability improves. Moreover, since an acid anhydride having specific solubility is used, the generation efficiency of nitrous acid during the use of the immunochromatographic device improves, and the substance to be detected can be detected with high sensitivity.

<Immunochromatographic Device>

The immunochromatographic device of the invention is an immunochromatographic device for extracting a substance to be detected with nitrous acid and is characterized by having the pad of the invention.

In a preferable embodiment, the immunochromatographic device of the invention is an immunochromatographic device for detecting a substance to be detected contained in a detection target in an analyte which contains a sample droplet receiving member, a labeling substance retaining member having a labeling substance containing part, a chromatography medium member having a detection part and an absorption member and which contains a nitrous acid compound and an acid anhydride having vapor pressure at 25° C. of $5 \times 10^{-2}$ Pa or less and solubility in water at 25° C. of 0.1 mg/L or more. The sample droplet receiving member, the labeling substance retaining member, the chromatography medium member and the absorption member are arranged in a manner that a sample develops in the members in this order. The immunochromatographic device has a part containing the nitrous acid compound and a part containing the acid anhydride at upstream positions from the detection part, and the part containing the acid anhydride is composed of the pad of the invention.

The term "member" and the term "part" used in this description have different meanings. For example, the "member containing the nitrous acid compound (the acid anhydride)" is defined as the entire "member" which contains the nitrous acid compound (the acid anhydride), while the "part containing the nitrous acid compound (the acid anhydride)" is defined as the area which actually contains the nitrous acid compound (the acid anhydride) in the member containing the nitrous acid compound (the acid anhydride). In this regard, the "part" sometimes refers to the entire member, not just a partial area of the member.

In this description, a member having a part containing the nitrous acid compound is sometimes called as a nitrous acid compound containing member, and a member having a part containing the acid anhydride is sometimes called as an acid anhydride containing member.

Figure 1:
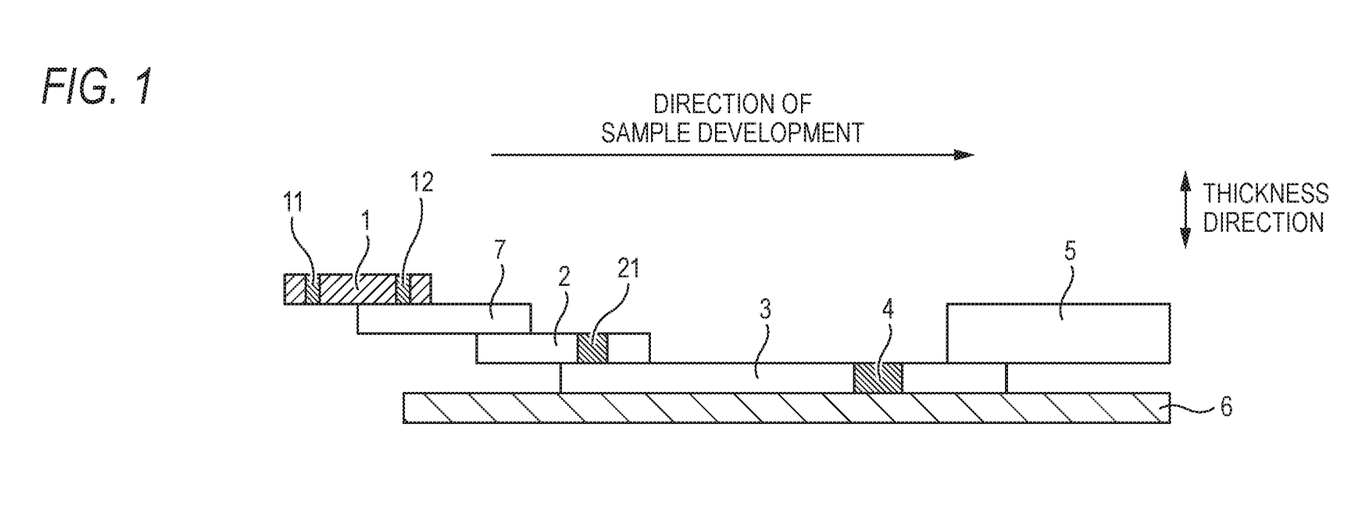
FIG. 1 is a cross section for explaining the structure of the immunochromatographic device of an embodiment of the invention.

In this description, the "direction of sample development" means the direction in which the sample develops (moves) before the sample is absorbed by the absorption member after dropping the sample to the sample droplet receiving member, and for example, the direction of sample development is the direction of the arrow (rightwards arrow) in the immunochromatographic device shown in FIG. 1. Also, the "upstream" in the invention means the opposite direction to the "direction of sample development" and means the direction to (side at) the sample droplet receiving member seen from the absorption member.

The immunochromatographic device of the invention is explained specifically below referring to the drawings.

As shown in FIG. 1, in an embodiment of the invention, the immunochromatographic device is composed of members including a sample droplet receiving member (1) having a sample droplet receiving part 11, an acid anhydride containing member (7) composed of the pad of the invention, a labeling substance retaining member (2) having a labeling substance containing part, a chromatography medium member (3) having a detection part (4) and an absorption member (5). In this embodiment, the sample droplet receiving member (1) has a part 12 containing nitrous acid compound, and the sample droplet receiving member (1) also has the function of a nitrous acid compound containing member.

In the device, the members constituting the immunochromatographic device are linked and arranged in a manner that the sample develops in the sample droplet receiving member (1), the acid anhydride containing member (7) composed of the pad of the invention, the labeling substance retaining member (2) having the labeling substance containing part, the chromatography medium member (3) having the detection part (4) and the absorption member (5) in this order. In this embodiment, another member may be between the members as long as the sample develops in the members in the order; and the sample droplet receiving member, the acid anhydride containing member, the labeling substance retaining member, the chromatography medium member and the absorption member do not have to be continuously connected to each other.

Figure 2:
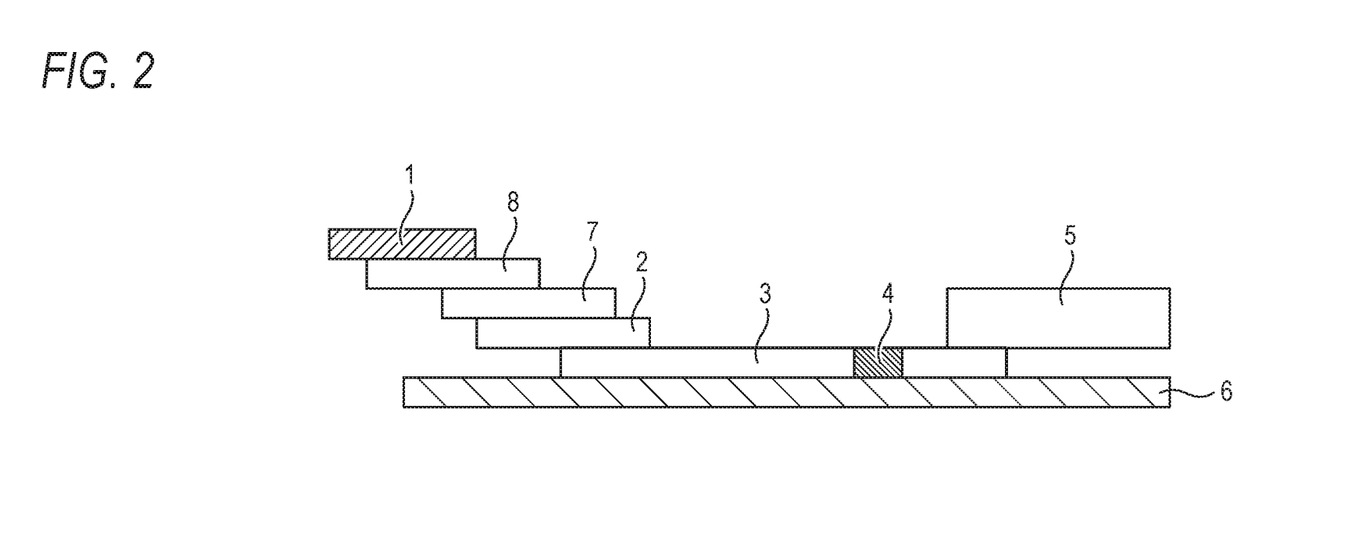
FIG. 2 is a cross section for explaining the structure of the immunochromatographic device of another embodiment of the invention.

As shown in FIG. 2, a part containing the nitrous acid compound may be provided separately as a nitrous acid compound containing member (8). As the nitrous acid compound containing member (8), glass fiber, cellulose membrane etc. are usually used. As a shape of the nitrous acid compound containing member (8), a sheet can be used.

The positions and the order of the acid anhydride containing member (7) and the nitrous acid compound containing member (8) may be any positions and any order as long as the members are at upstream positions from the detection part (4). For example, the acid the anhydride containing member (7) and the nitrous acid compound containing member (8) can be independently at an upstream position or a downstream position from the labeling substance retaining member (2)

According to the need, the pad of the invention can be used as the sample droplet receiving member (1) without providing the acid anhydride containing member (7). Moreover, although the part 12 containing the nitrous acid compound may be on the acid anhydride containing member (7), the part 12 containing the nitrous acid compound and the part containing acid anhydride are not at the same positions.

Regarding the embodiments in which the members are linked, the members may be linked in a manner that the members overlap each other as shown in FIG. 1, or the members do not overlap each other but are linked in a manner that the sides of the members are in contact with each other in the direction of sample development.

The acid anhydride containing member (7) can be composed of a porous sheet. Examples of the porous sheet include cellulose filter paper, recycled cellulose filter paper, glass fiber filter paper, polyurethane, polyacetate, cellulose acetate, nylon, cotton cloth and the like. Regarding the shape of the acid anhydride containing member (7), a sheet can be used.

The sample droplet receiving member (1) means a member having a part to which a sample containing an analyte (sometimes simply called a "sample" below) is dropped (sometimes simply called the "sample droplet receiving part 11" below) in the immunochromatographic device and is the member indicated with reference number 1 in FIG. 1.

The sample droplet receiving part 11 refers to a partial area to which the sample is dropped in the sample droplet receiving member (1). The position of the sample droplet receiving part 11 in the sample droplet receiving member (1) is not particularly limited and may be, for example, at or around an end of the sample droplet receiving member (1) or in or around the middle of the sample droplet receiving member (1). The sample droplet receiving member (1) can contain any reagent which does not impair the effects of the invention.

The sample droplet receiving part 11 is generally at an upstream position from the part 12 containing the nitrous acid compound.

The sample droplet receiving member (1) can be composed of a porous sheet having the properties of rapidly absorbing the sample but allowing the sample to move rapidly with weak holding power. Examples of the porous sheet include cellulose filter paper, recycled cellulose filter paper, glass fiber filter paper, polyurethane, polyacetate, cellulose acetate, nylon, cotton cloth and the like. Regarding the shape of the sample droplet receiving member (1), a sheet can be used.

The labeling substance retaining member (2) is a member having a part containing a labeling substance obtained by labeling a reagent component with a labeling component (sometimes simply called a "labeling substance containing part 21" below) and is the member indicated with reference number 2 in FIG. 1.

The labeling substance containing part 21 refers to an area which actually contains the labeling substance in the labeling substance retaining member (2). The labeling substance containing part 21 may occupy a partial area of the labeling substance retaining member (2) as shown in FIG. 1 or occupy the entire area of the labeling substance retaining member (2).

When the labeling substance containing part 21 occupies a partial area of the labeling substance retaining member (2), the position of the labeling substance containing part 21 in the labeling substance retaining member (2) is not particularly limited and may be, for example, at or around an end of the labeling substance retaining member (2) or in or around the middle of the labeling substance retaining member (2). The labeling substance retaining member (2) can contain any reagent which does not impair the effects of the invention.

Examples of the labeling component include metal particles, latex particles, an enzyme, a fluorescent compound and the like, and metal particles are preferable of these examples. The reagent component is composed of particles or molecules which are capable of recognizing the analyte and is preferably a monoclonal antibody, a polyclonal antibody or a fragment thereof (a first reagent).

As the metal particles, particles of a single noble metal such as gold, silver, platinum, germanium, rhodium and palladium and composite particles of noble metals can be preferably used. Of these examples, gold is sensitive to a change in hues and thus is particularly preferable.

The average particle diameter of the metal particles is preferably from 1 nm to 500 nm, more preferably from 10 nm to 250 nm, and further preferably from 35 nm to 100 nm. Nano-sized gold particles having such an average particle diameter are called gold nanoparticles.

In the immunochromatographic detection method, taking the particle diameter of gold, its particle size distribution, its color and the like into consideration, gold composite particles in which platinum particles are supported on the surface of gold particles can be used as a label for the immunochromatographic detection method or used to improve the utility as a dye agent for proteins. When a so-called sensitizer such as a gold label amplifier having a functional group which can bind to the surface of the metal particles and a reactive group which can bind to the antibody is used, the measurement sensitivity can be enhanced.

For the labeling substance retaining member (2), for example, a membrane of glass fibers or cellulose or the like is usually used. Regarding the shape of the labeling substance retaining member (2), a sheet can be used.

In the embodiment shown in FIG. 1, the nitrous acid compound and the acid anhydride can react with each other and generate nitrous acid at an upstream position from the labeling substance containing part 21, and the substance to be detected can be extracted from the detection target. Accordingly, the detection target can move to the labeling substance containing part 21 in the state in which the substance to be detected is extracted, and the substance to be detected can be labeled.

Figure 3:
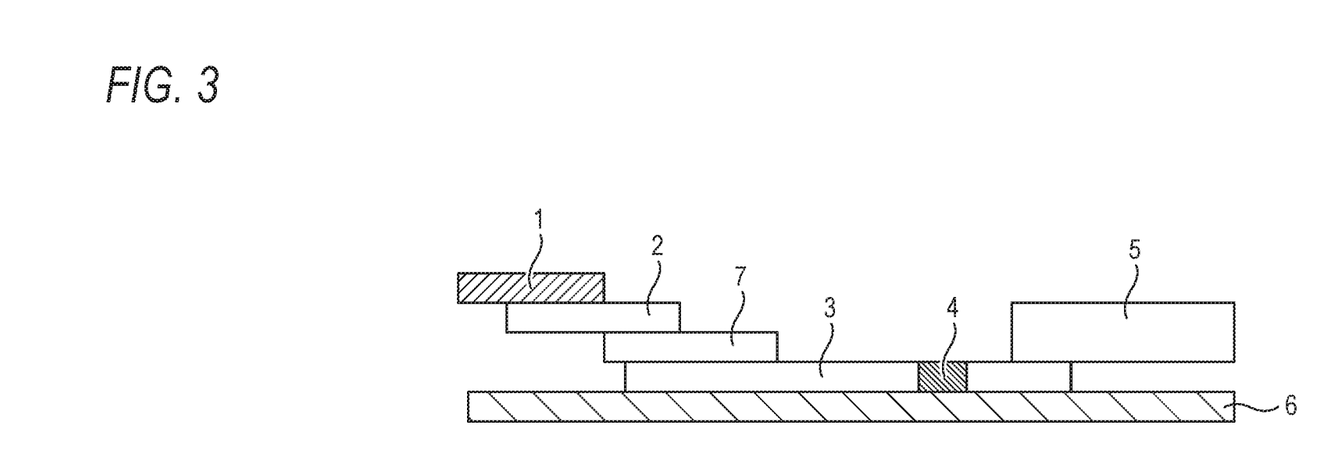
FIG. 3 is a cross section for explaining the structure of the immunochromatographic device used in the Examples.

In the embodiment shown in FIG. 3, the part 12 (not shown in the figure) containing the nitrous acid compound is at an upstream position from the labeling substance retaining member (2), and the part containing the acid anhydride is at a downstream position from the labeling substance retaining member (2). When the sample is dropped to the sample droplet receiving member (1), the sample moves to the acid anhydride containing member (7) with the nitrous acid compound contained in the sample droplet receiving member (1) and with the labeling substance. Then, in the acid anhydride containing member (7), nitrous acid is generated through reaction of the nitrous acid compound and the acid anhydride, and the substance to be detected is labeled with the labeling substance at the same time as the substance to be detected is extracted from the sample.

The embodiment in which the part 12 containing the nitrous acid compound is at an upstream position from the labeling substance retaining member (2) and in which the acid anhydride containing part is at a downstream position from the labeling substance retaining member (2) is preferable since the substance to be detected can be labeled with the labeling substance at the same time as the substance to be detected is extracted from the sample, which results in a decrease in the loss of the labeling substance which does not bind to the substance to be detected and in improvement of the detection sensitivity.

In the invention, the part containing the nitrous acid compound and the part containing the acid anhydride can also be arranged in a manner that the parts are not substantially in contact with each other in the thickness direction. Here, the "thickness direction" means the direction of the thicknesses of the members described above in the immunochromatographic device of the invention. When the members are sheets, the thickness direction refers to the thickness direction of the sheets. For example, in the immunochromatographic device shown in FIG. 1, the thickness direction is the direction of the arrow (up down arrow). The "contact"

means the physical contact between the part containing the nitrous acid compound and the part containing the acid anhydride. That "the part containing the nitrous acid compound and the part containing the acid anhydride are not substantially in contact with each other in the thickness direction" means that the length in the direction of sample development of the area of the contact between the part containing the nitrous acid compound and the part containing the acid anhydride in the thickness direction is 0.5 mm or less.

The nitrous acid compound in the invention is not particularly limited as long as the nitrous acid compound generates nitrous acid by reacting with an acid and does not adversely affect the test. The nitrous acid compound is preferably a nitrite. Examples of the nitrite include inorganic nitrites such as sodium nitrite, potassium nitrite, calcium nitrite and magnesium nitrite and organic nitrous acid compounds such as methyl nitrite, ethyl nitrite, butyl nitrite and amyl nitrite. A mixture thereof may also be used. The nitrous acid compound is preferably an inorganic nitrite, especially preferably an alkali metal salt of nitrous acid, and most preferably sodium nitrite.

The amount of the nitrous acid compound in the immunochromatographic device of the invention is preferably from 12.5 µmol/device to 160 µmol/device, and more preferably from 50 µmol/device to 100 µmol/device, in view of the improvement of the detection sensitivity. Additionally, the amount of the nitrous acid compound per unit area in the part containing the nitrous acid compound is preferably from 12.5 µmol/cm$^2$ to 160 µmol/cm$^2$ and more preferably from 50 µmol/cm$^2$ to 100 µmol/cm$^2$. By having such content, extraction efficiency of the detection target becomes higher and as a result, detection sensitivity of the detection target can be further improved.

The chromatography medium member (3) is obtained by producing the detection part (4) on a membrane support. The membrane support is not particularly limited as long as the membrane support can absorb and move the sample through a capillary phenomenon.

The chromatography medium member (3) can be selected, for example, from the group consisting of nitrocellulose, cellulose acetate, nylon, polyether sulfones, polyvinyl alcohol, polyesters, glass fibers, polyolefins, cellulose and artificial polymers of mixed fibers thereof. Regarding the shape of the chromatography medium member (3), a sheet can be used.

In the detection part (4), a monoclonal antibody, a polyclonal antibody or a fragment thereof (a second reagent) is supported and immobilized on a nitrocellulose sheet.

Filter paper composed of glass fibers, cellulose fibers or the like, which is a material capable of rapidly absorbing the excess sample, is generally used for the absorption member (5), but a material which is further capable of holding the absorbed liquid to prevent the backflow is more preferably used (JP-A-2012-189346). Regarding the shape of the absorption member (5), a sheet can be used.

Moreover, as described above, members other than those described above may be at any positions of the device of the invention. The members can be each composed of a porous sheet having the properties of rapidly absorbing the sample but allowing the analyte (analyte sample) to move rapidly with weak holding power.

Examples of the porous sheet include cellulose filter paper, recycled cellulose filter paper, glass fiber filter paper, polyurethane, polyacetate, cellulose acetate, nylon, cotton cloth and the like. Regarding the shapes of the members, sheets can be used.

The immunochromatographic device of the invention can include a backing sheet (6). The backing sheet (6) is a base material. One surface of the backing sheet (6) is adhesive since an adhesive is applied on the surface or an adhesive tape is attached. The members are partially or entirely closely adhered and provided on the adhesive surface.

The base material is not particularly limited as long as the backing sheet (6) is not permeable or moisture impermeable with respect to the sample solution due to the adhesive.

One or both of the reagent component used for the detection part (4) (the second reagent) and the reagent component used for the labeling reagent (the first reagent) may be a monoclonal antibody or a polyclonal antibody. It is preferable that the reagent component used for the detection part (4) (the second reagent) is a polyclonal antibody and that the reagent component used for the labeling reagent (the first reagent) is a monoclonal antibody.

The monoclonal antibodies, the polyclonal antibodies and the fragments thereof are known and available and can be prepared by known methods. Examples of the kinds of animal producing the antibodies include human, mouse, rat, rabbit, goat, horse and the like. The immunoglobulin may be any of IgG, IgM, IgA, IgE and IgD.

In particular, it is preferable to use a rabbit-derived antibody for both of the reagent component used for the labeling substance retaining member (2) (the first reagent) and the reagent component used for the detection part (4) (the second reagent).

<Immunochromatographic Kit>

The immunochromatographic kit of the invention includes the immunochromatographic device and an analyte dilution solution for diluting an analyte.

In the immunochromatographic kit of the invention, the analyte dilution solution can be used also as a development solution. When the analyte dilution solution is used as a development solution, an solution containing the analyte obtained by mixing the analyte and the analyte dilution solution (development solution) can be supplied/dropped as a sample to the sample droplet receiving member for development. Alternatively, the analyte dilution solution (development solution) may be supplied or dropped to the sample droplet receiving member for development after supplying/dropping the analyte to the sample droplet receiving member in advance.

In general, when the pH condition of the development solution is an acidic condition, the efficiency of generation of nitrous acid generated through reaction of the nitrous acid compound and the acid anhydride is high, and the extraction efficiency of the antigen can be improved. An acidic pH condition, however, may cause problems, such as the precipitation of proteins including for example casein or salts thereof contained in the immunochromatographic device or in the analyte dilution solution described below, highly viscous proteins contained in the analyte and the like and improper development due to the agglutination of the labeling substance.

Accordingly, the pH condition of the development solution in the invention is preferably pH at which nitrous acid is generated and pH at which the proteins such as casein, the highly viscous proteins contained in the analyte and the like are not precipitated and at which the agglutination of the labeling substance is not caused. As the pH condition, pH is from 6.5 to 8.5, preferably from 6.6 to 8.0, and most preferably from 6.8 to 7.5. At the pH, the deposition of the proteins or the agglutination of the labeling substance is not easily caused.

In the immunochromatographic kit of the invention, the analyte dilution solution and the parts of the immunochromatographic device can contain reagents such as a surfactant including a nonionic surfactant or the like, a salt, a buffer and an additive in addition to the reagents described above within the scope which do not impair the effects of the invention.

Examples of the nonionic surfactant which can be used for the immunochromatographic kit of the invention include polyoxyethylene alkyl ethers, polyoxyethylene/polyoxypropylene alkyl ethers, polyoxyethylene sorbitan fatty acid esters (product name "Tween" series), polyoxyethylene p-t-octylphenyl ether (product name "Triton" series), polyoxyethylene p-t-nonylphenyl ether (product name "Triton N" series), alkyl polyglucosides, fatty acid diethanol amides, alkyl monoglyceryl ethers and the like. An ionic surfactant other than the nonionic surfactant or the like can also be added and used within the scope that does not cause any adverse effects.

The amount of the nonionic surfactant used for the analyte dilution solution or the immunochromatographic device of the invention is, per one device, preferably in the range of 0.24 mg to 2.4 mg, and the nonionic surfactant can be more preferably contained in an amount in the range of 0.6 mg to 1.8 mg.

An amount of less than 0.24 mg per one device has a tendency towards instable development, making it impossible to make accurate determination, or has a tendency towards difficulty in accurate determination since nonspecific reaction cannot be inhibited. A concentration exceeding 2.4 mg per one device is higher than needed and does not affect preferably on the inhibition of nonspecific reaction. Moreover, such an amount has no technical meanings, is not economical and is a waste.

Typical examples of the salt used for the analyte dilution solution or the immunochromatographic device of the invention include sodium chloride, potassium chloride, calcium chloride, magnesium chloride and the like. Sodium chloride is preferable.

The concentration of the salt used for the analyte dilution solution or the immunochromatographic device of the invention is, per one device, preferably in the range of 1 mM to 500 mM, more preferably in the range of 5 mM to 200 mM, and further preferably in the range of 10 mM to 50 mM. When the concentration is lower than 1 mM, for example as low as around 0.1 mM, the effect of extracting a protein becomes insufficient. An amount exceeding 500 mM, for example as high as 1 M or 2 M, has no technical meanings. Such a concentration is higher than needed, is not economical and is a waste.

Not only one kind but also two or more kinds can be added and used as the salt used for the analyte dilution solution or the immunochromatographic device of the invention.

The buffer used for the analyte dilution solution or the immunochromatographic device of the invention is not particularly limited as long as the buffer has an effect (buffering effect) of causing no fatal effect even when the concentration changes due to addition of the sample or evaporation or dilution of the sample or when small amounts of foreign substances contaminate from the outside.

In the invention, examples of the buffer include phosphate buffer (phosphoric acid+sodium phosphate), acetate buffer (acetic acid+sodium acetate), citrate buffer (citric acid+sodium citrate), borate buffer, tris-hydrochloric acid buffer (tris(hydroxymethyl)aminomethane+hydrochloric acid), TE buffer (tris+ethylenediaminetetraacetic acid), TAE buffer (tris+acetic acid+ethylenediaminetetraacetic acid), TBE buffer (tris+boric acid+ethylenediaminetetraacetic acid), HEPES buffer (2-[4-(2-hydroxyethyl)-1-piperazinyl] ethanesulfonic acid), Bicine buffer (N,N-bis(2-hydroxyethyl) glycine buffer) and the like.

The buffer is preferably phosphate buffer, tris-hydrochloric acid buffer, acetate buffer or the like, more preferably tris-hydrochloric acid buffer. In the immunochromatographic detection system of the invention, two or more kinds of buffer can be used, without any restriction, within the scope which does not cause any adverse effects.

The concentration of the buffer used in the invention is, per one device, preferably in the range of 10 mM to 500 mM, more preferably in the range of 10 mM to 300 mM, and further preferably in the range of 30 mM to 100 mM.

When the concentration is lower than 10 mM, the buffering effect becomes insufficient, and the precipitation of the protein components and the agglutination of the labeling particles are not inhibited sufficiently. A concentration exceeding 500 mM is higher than needed, is not economical and is a waste.

The optimum pH range of the buffer is 7.1 to 9.8.

In the analyte dilution solution or the immunochromatographic device of the invention, it is also possible and effective to add and use, without any restriction, a kind or two or more kinds of additives which are known to inhibit side reaction based on biological affinity or inhibit nonspecific reaction, such as proteins (for example, bovine serum albumin, gelatin, casein and the like), polymer compounds (for example, polyethylene glycol, methyl cellulose, polyvinylpyrrolidone, polyvinyl alcohol, dextran and the like), ionic surfactants or polyanions (for example, dextran sulfate, heparin, polystyrene sulfonate, chondroitin sulfate and the like), which are for promoting antigen-antibody reaction or inhibiting nonspecific reaction, antibacterial agents and the like.

It is also possible and effective that, without any restriction, a kind or two or more kinds of the proteins, the polymer compounds, the ionic surfactants or the polyanions, which are for promoting antigen-antibody reaction or inhibiting nonspecific reaction, the antibacterial agents and the like are retained on the path of the mobile phase on the chromatography medium member constituting the stationary phase.

The concentrations of the additives contained in the analyte dilution solution or the immunochromatographic device of the invention are, per one device, preferably in the range of 0.01% by mass to 20% by mass, more preferably in the range of 0.1% by mass to 10% by mass, and further preferably in the range of 0.5% by mass to 5% by mass. When the concentrations are lower than 0.01% by mass, nonspecific reaction cannot be inhibited, and accurate determination cannot be made. A concentration exceeding 20% by mass is higher than needed, is not economical and is a waste.

Water is usually used as a solvent of the analyte dilution solution. Moreover, in addition to the nonionic surfactant, the salt, the buffer and the like, a kind or two or more kinds of the following materials may be added: a protein, a polymer compound (such as PVP), an ionic surfactant or a polyanion for promoting antigen-antibody reaction or inhibiting nonspecific reaction; an antibacterial agent; a chelating agent; and the like.

The order of addition is not particularly limited, and simultaneous addition is also acceptable. An solution containing the analyte obtained by mixing the analyte to be detected and the analyte dilution solution can be supplied/dropped to the sample droplet receiving member for development, or the analyte dilution solution may be supplied/dropped to the sample droplet receiving member for development after supplying/dropping the analyte to the sample droplet receiving member in advance.

When the immunochromatographic device contains any reagent, the reagent is applied to the part which should contain the reagent and then dried, or the part is impregnated with the reagent and then dried, in an example method. By such a method, an embodiment in which the reagent is supported or held in the part can be achieved.

When the reagent is contained in a part of a member as a spot, not in the entire member, for example, a method of masking the member and then spraying the reagent or the like may be used.

The principles of the determination in a typical kit structure of the invention are explained in 1 to 6 below. The following explanation is based on the device of FIG. 1 as an example.

1. A certain amount (usually 0.1 mL to 2.0 mL) of an solution containing the analyte obtained by diluting an analyte with the analyte dilution solution is dropped as a sample to the sample droplet receiving member (1) (the sample droplet receiving part 11) of the immunochromatographic device. When the solution containing analyte is dropped, the solution containing analyte is rapidly absorbed by the sample droplet receiving member (1) and immediately starts to move to the acid anhydride containing member (7).

2. The nitrous acid compound, which is retained in the part 12 containing the nitrous acid compound provided in the sample droplet receiving member (1), dissolves in the water content of the solution containing analyte which has moved to the position and moves with the analyte.

3. Next, the solution containing analyte containing the dissolved nitrous acid compound comes into contact with the acid anhydride retained in the acid anhydride containing member (7), and the nitrous acid compound and the acid anhydride react with each other and generate nitrous acid. The nitrous acid extracts the substance to be detected contained in the detection target in the analyte.

4. Next, in the labeling substance retaining member (2), the extracted substance to be detected is labeled with the labeling reagent (the first reagent) retained in the labeling substance containing part 21 and moves with the analyte.

5. Next, the labeling reagent dissolved in the water content of the solution containing analyte passes through the detection part (4) on the chromatography medium member (3). Here, when the substance to be detected is contained in the solution containing analyte, the substance to be detected is immobilized in the detection part due to specific antigen-antibody binding reaction in a manner that the substance to be detected is sandwiched between the antibody (the second reagent) supported and immobilized in the detection part (4) and the labeling reagent (the first reagent), and the detection part (4) is colored. In this manner, the detection target can be detected. When the substance to be detected is not contained in the analyte, the specific binding reaction does not occur even when the labeling reagent (the first reagent) dissolved in the water content of the solution containing analyte passes through the detection part (4) on the chromatography medium member (3), and thus the detection part (4) is not colored.

6. At the end, the solution containing analyte moves to the absorption member (5) and is absorbed.

In this manner, the presence or absence of the substance to be detected in the analyte can be accurately determined.

<Immunochromatographic Detection Method>

The immunochromatographic detection method of the invention includes the following (i) to (v) and detects a detection target in an analyte using the immunochromatographic kit.

(i) Dropping an solution containing the analyte obtained by diluting the analyte with the analyte dilution solution to the sample droplet receiving member.

(ii) Extracting a substance to be detected from the detection target in the analyte with nitrous acid generated through reaction of the nitrous acid compound and the acid anhydride.

(iii) Labeling the substance to be detected in the labeling substance retaining member.

(iv) Allowing the solution containing analyte to move on the chromatography medium member and detecting the detection target in the detection part.

(v) Absorbing the solution containing analyte with the absorption member.

The details of the (i) to (v) are the same as the contents described above for the principles of the determination.

Although the embodiments of the invention are further explained below referring to Examples and Comparative Examples, the invention is not limited to the Examples.

Example 1

<Production of Immunochromatographic Kit>

In this Example, an immunochromatographic kit including an analyte dilution solution and an immunochromatographic device having a sample droplet receiving member (1) containing sodium nitrite, a labeling substance retaining member (2), an acid anhydride containing member (7) containing bicyclo[2,2,2]oct-7-ene-2,3,5,6-tetracarboxylic dianhydride, a chromatography medium member (3) having a detection part (4) and an absorption member (5) which were arranged in a manner that a sample would develop in the members in this order was produced.

(1) Formation of Detection Part (4) on Chromatography Medium Member (3)

A sheet composed of nitrocellulose (manufactured by Millipore Corporation, product name: HF120, 250 mm×25 mm) was used as a membrane. A rabbit-derived anti-hemolytic *streptococcus* polyclonal antibody (the second reagent) (manufactured by Meridian Inc.) was diluted to a concentration of 1.0 mg/mL with a 10 mM phosphate buffer (pH 7.4) containing 5% by mass of isopropanol, and 150 μL of the diluted solution was applied with a width of 1 mm onto the membrane using an antibody applicator (manufactured by BioDot), dried at 50° C. for 30 minutes and dried at room temperature overnight. The detection part (4) was thus formed on the chromatography medium member (3).

(2) Production of Labeling Substance Solution

To 0.9 mL of a colloidal gold suspension (manufactured by Tanaka Kikinzoku Kogyo K.K.: average particle diameter of 40 nm), 0.1 mL of a rabbit-derived anti-hemolytic *streptococcus* monoclonal antibody (manufactured by Virostat Inc.) which had been diluted to a concentration of 0.03 mg/mL with a 50 mM phosphate buffer (pH 7.5) was added, and the mixture was left to stand still at 4° C. for 10 minutes.

Then, 0.1 mL of a 50 mM phosphate buffer (pH 7.5) containing 0.01% by mass of polyethylene glycol with a thiol group at one terminus (manufactured by Nippon Oil & Fats Co., Ltd., molecular weight of 20,000) was added. After stirring thoroughly, the mixture was centrifuged at 15,000 G for 5 minutes, and the supernatant was removed. Then, 0.1 mL of a 20 mM tris buffer (pH 8.0) containing 1% by mass of bovine serum albumin was added. A labeling substance solution was thus produced.

(3) Production of Sample Droplet Receiving Member (1) Containing Sodium Nitrite

A 3M aqueous sodium nitrite solution in an amount of 0.5 mL was applied to a glass fiber pad of 20 mm×100 mm (manufactured by Millipore Corporation) and dried with a dryer under reduced pressure at room temperature for four hours, and the sample droplet receiving member (1) containing sodium nitrite was thus produced. The amount of sodium nitrite contained in the sample droplet receiving member (1) was 1.5 mmol. Additionally, it was 75 μmol/cm².

(4) Production of Acid Anhydride Containing Member (7)

Bicyclo[2,2,2]oct-7-ene-2,3,5,6-tetracarboxylic dianhydride was dissolved in diethylformamide to a concentration of 50 mM. A glass fiber pad of 20 mm×100 mm (manufactured by Millipore Corporation) was impregnated with the prepared solution and dried under reduced pressure for 24 hours, and the acid anhydride containing member (7) was thus produced. The amount of bicyclo[2,2,2]oct-7-ene-2,3,5,6-tetracarboxylic dianhydride contained in the acid anhydride containing member (7) was 20 μmol. Additionally, it was 1 μmol/cm².

(5) Production of Immunochromatographic Device

A solution obtained by adding 50 μL of a 30% by mass of aqueous trehalose solution and 400 μL of deionized water to 50 μL of the labeling substance solution produced above was evenly applied to a glass fiber pad of 8 mm×150 mm (manufactured by Millipore Corporation) and then dried with a dryer under reduced pressure at room temperature for four hours, and the labeling substance retaining member (2) was thus produced.

Next, the sample droplet receiving member (1), the labeling substance retaining member (2), the acid anhydride containing member (7), the chromatography medium member (3) having the detection part (4) and the absorption member (5) were pasted to a base material composed of a backing sheet (6) in a manner that the members were linked in this order along the direction of sample development, and the device used in Example 1 was thus obtained (the order shown in FIG. 3).

Subsequently, the obtained product was cut with a width of 5 mm with a cutter, and an immunochromatographic device was thus obtained. The amount of sodium nitrite contained in the sample droplet receiving member (1) in the device was 75 μmol and 75 μmol/cm². Additionally, the amount of the acid anhydride contained in the acid anhydride containing member (7) in the device was 1 μmol and is 1 μmol/cm².

(6) Production of Analyte Dilution Solution

An analyte dilution solution which contained a 20 mM tris buffer (pH 8.0) containing 0.5% by mass of Tween 20, 0.6% by mass of polyvinylpyrrolidone (average molecular weight of 360,000), 1% by mass of bovine serum albumin and 150 mM sodium chloride and which was for diluting an analyte and dropping the analyte to an immunochromatographic device for development was obtained.

<Measurement>

The immunochromatographic device and the analyte dilution solution produced above were used, and a sample obtained by adding inactivated Group A β-hemolytic *streptococcus* at 5×10⁵ org/mL was used as a positive analyte sample.

The analyte sample in an amount of 150 μL was dropped to the sample droplet receiving part of the device and developed, and a visual evaluation was made after 5 minutes. Any of the following marks was given: "+" (positive) when the red line on the detection part (4) could be visually observed; "++" (strong positive) when the red line could be visually observed clearly; "±" (weak positive) when a light red line could be visually observed; and "−" (negative) when the red line could not be visually observed. The results are shown in Table 1.

Separately from the above evaluation, the immunochromatographic device produced above were stored at 50° C. for 24 hours, and then the measurement and the visual evaluation were conducted. The results are shown in Table 1.

Measurement was also conducted using the analyte dilution solution which did not contain the hemolytic *streptococcus* as a negative analyte sample. It was confirmed that all the examples were negative.

Whether the acids used in the Examples and the Comparative Examples sublimate at 25° C. at 20 Pa was examined by the following method. First, 1 g of an acid was measured in a glass vial, and the weight was measured after subjecting the acid to reduced pressure at 25° C. at 20 Pa for 12 hours. It was determined that the acid did not sublimate when the increase or the decrease in the weight was within 5%, and it was determined that the acid sublimated when the increase or the decrease in the weight exceeded 5%. The results are shown in Table 1. In Table 1, "A" indicates that the acid did not sublimate, and "B" indicates that the acid sublimated. The mark "−" indicates that the acid was not evaluated.

The vapor pressures at 25° C. and the solubilities in water at 25° C. of the acids used in the Examples and the Comparative Examples are the values of databases (calculated values). The mark "−" in Table 1 indicates that the value is not known.

Figure 4:
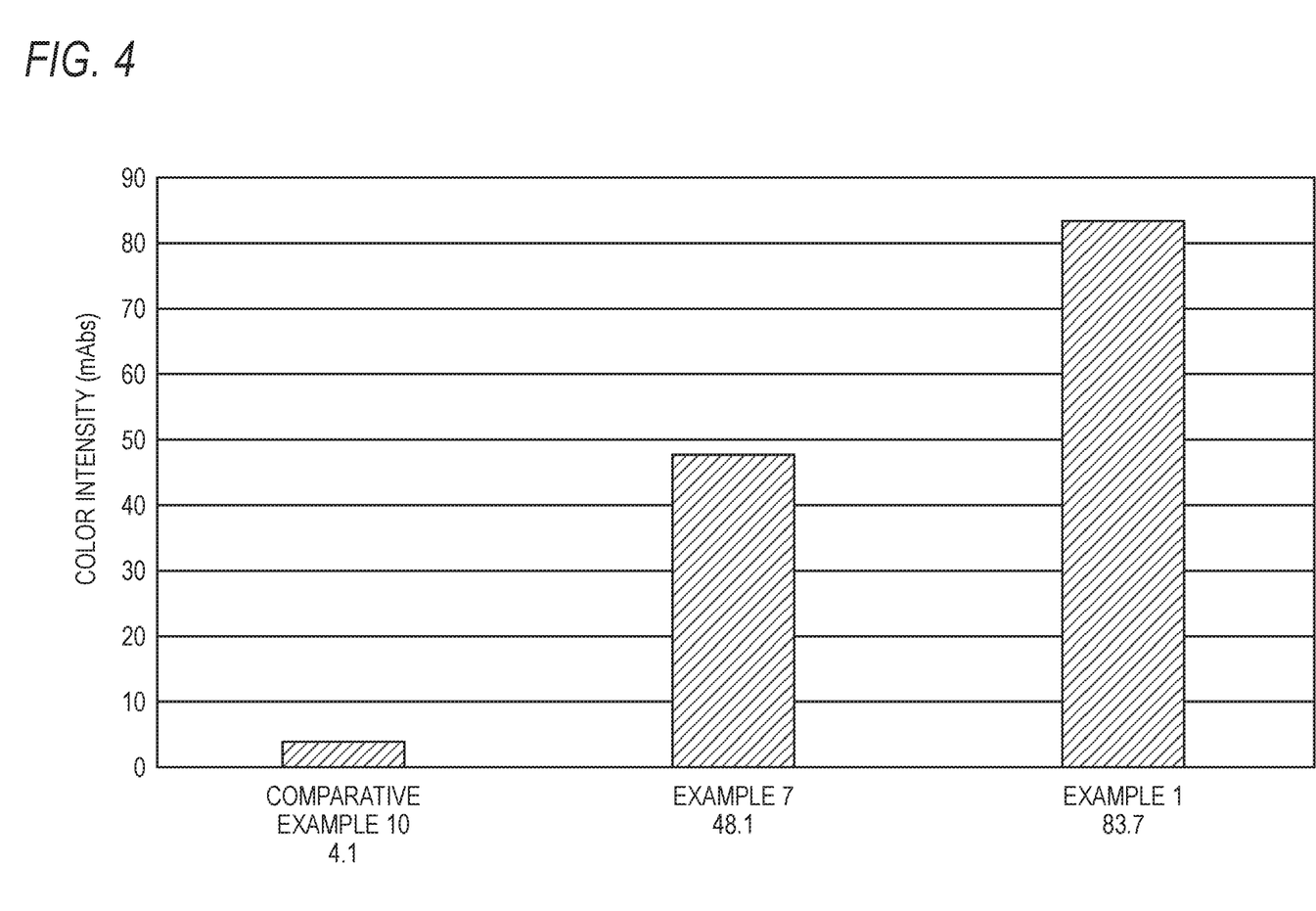
FIG. 4 is a graph showing the results of the color intensities of the red lines of the detection parts (4) measured in Example 1, Example 7 and Comparative Example 10.

The color intensity of the red line on the detection part (4) five minutes after starting development was measured with an immunochromatoreader (manufactured by Hamamatsu Photonics K.K.). As a result, the color intensity was 83.7 mAbs. A graph showing the results is shown in FIG. 4.

Example 2 to Example 6, Reference Example 1, Reference Example 2, and Comparative Example 1 to Comparative Example 9

Immunochromatographic kits were produced and measurement was conducted in the same manners as in Example 1 except that the kind of the acid anhydride in Example 1 was changed to those shown in Table 1. The results are shown in Table 1.

Example 7

An immunochromatographic kit was produced in the same manner as in Example 1 except that the sample droplet receiving member (1), the acid anhydride containing member (7), the labeling substance retaining member (2), the chromatography medium member (3) having the detection part (4) and the absorption member (5) were pasted to a base material composed of a backing sheet (6) in a manner that the members were linked in this order along the direction of sample development (the order shown in FIG. 1), and the color intensity was measured with an immunochromatoreader (manufactured by Hamamatsu Photonics K.K.). As a result, the color intensity after five minutes was 48.1 mAbs. A graph showing the results is shown in FIG. 4.

Comparative Example 10

An immunochromatographic kit was produced in the same manner as in Example 3 except that "malic acid" was used instead of "bicyclo[2,2,2]oct-7-ene-2,3,5,6-tetracarboxylic dianhydride", which is the acid anhydride, and the color intensity after five minutes was measured with an immunochromatoreader (manufactured by Hamamatsu Photonics K.K.). As a result, the color intensity was 4.1 mAbs. A graph showing the results is shown in FIG. 4.

Examples 1, 2, 5, and 6 wherein the pad containing acid anhydride having two or more acid anhydride groups per a molecule were used.

REFERENCE SIGNS LIST

1. Sample droplet receiving member
11. Sample droplet receiving part
12. Part containing nitrous acid compound
2. Labeling substance retaining member
21. Labeling substance containing part
3. Chromatography medium member
4. Detection part
5. Absorption member
6. Backing sheet

TABLE 1

| Example | Compound Name | Acid Content per one pad (μmol) | Vapor Pressure at 25° C. (Pa) | Sublimation at 25° C. at 20 Pa | Solubility in Water at 25° C. (mg/L) | Result of Visual Evaluation (After 5 Minutes) | Result of Visual Evaluation (After Storage at 50° C. for 24 Hours) |
|---|---|---|---|---|---|---|---|
| Example 1 | bicyclo[2,2,2]oct-7-ene-2,3,5,6-tetracarboxylic dianhydride | 1 | $2.3 \times 10^{-3}$ | A | $3.4 \times 10^3$ | ++ | ++ |
| Example 2 | pyromellitic anhydride | 1 | $2.0 \times 10^{-3}$ | A | $6.0 \times 10$ | ++ | ++ |
| Example 3 | 4-(1-propynyl)phthalic anhydride | 1 | $3.2 \times 10^{-2}$ | A | $1.8 \times 10^2$ | + | + |
| Example 4 | 3-acetamidophthalic anhydride | 1 | $1.2 \times 10^{-4}$ | A | $8.6 \times 10^2$ | + | + |
| Example 5 | 1,2,4,5-cyclohexanetetracarboxylic dianhydride | 1 | $1.8 \times 10^{-2}$ | A | $3.3 \times 10^3$ | ++ | ++ |
| Example 6 | 4-(2,5-dioxotetrahydrofuran-3-yl)-1,2,3,4-tetrahydronaphthalene-1,2-dicarboxylic anhydride | 1 | $2.1 \times 10^{-5}$ | A | $1.9 \times 10^1$ | ++ | ++ |
| Reference Example 1 | tetrapropenylsuccinic anhydride | 1 | $8.1 \times 10^{-3}$ | A | $6.4 \times 10^{-2}$ | ± | + |
| Reference Example 2 | octadecenylsuccinic anhydride | 1.9 | $3.6 \times 10^{-4}$ | A | $6.2 \times 10^{-5}$ | ± | ± |
| Comparative Example 1 | N-(benzoyloxy)succinimide | 1 | $7.9 \times 10^{-6}$ | — | — | − | − |
| Comparative Example 2 | succinic anhydride | 5.6 | $2.4 \times 10^{-1}$ | B | — | ++ | − |
| Comparative Example 3 | malic acid | 20 | — | — | — | − | − |
| Comparative Example 4 | itaconic acid | 20 | — | — | — | − | − |
| Comparative Example 5 | N,N-bis(2-hydroxyethyl)glycine | 20 | — | — | — | − | − |
| Comparative Example 6 | oleic acid | 20 | — | — | — | − | − |
| Comparative Example 7 | glutamic acid | 1 | — | — | — | − | − |
| Comparative Example 8 | phenylsussinic acid anhydride | 1 | $6.0 \times 10^{-1}$ | A | $4.7 \times 10^2$ | + | − |
| Comparative Example 9 | cis-4-cyclohexene-1,2-dicarboxylic anhydride | 1 | 7.7 | A | $1.6 \times 10^3$ | + | − |

As shown in Table 1 and FIG. 4, the immunochromatographic devices of the Examples had improved storage stability and improved detection sensitivity in comparison with those of the Comparative Examples since pads containing an acid anhydride having specific vapor pressure and specific solubility instead of the conventional organic acids were used. Particularly, further good results were obtained in 7. Acid anhydride containing member
8. Nitrous acid compound containing member

What is claimed is:
1. A pad used for an immunochromatographic device for extracting a substance to be detected contained in a detection target in an analyte with nitrous acid, comprising:
an acid dianhydride having vapor pressure at 25° C. of $5 \times 10^{-2}$ Pa or less and solubility in water at 25° C. of 0.1 mg/L or more, wherein the pad is impregnated with the acid dianhydride, and the pad is in fluid communication with a sample droplet receiving member of the immunochromatographic device, at an upstream position or downstream position from a labeling substance retaining member, wherein the acid dianhydride is one or more selected from the group consisting of bicyclo[2,2,2]oct-7-ene-2,3,5,6-tetracarboxylic dianhydride and 1,2,4,5-cyclohexanetetracarboxylic dianhydride.

2. The pad according to claim 1, wherein the vapor pressure at 25° C. of the acid dianhydride is $2\times10^{-2}$ Pa or less.

3. The pad according to claim 1, wherein a content of the acid dianhydride in the pad is 0.4 µmol to 8.4 µmol, per one pad.

4. An immunochromatographic device for extracting a substance to be detected contained in a detection target in an analyte with nitrous acid, comprising the pad according to claim 1.

5. The immunochromatographic device for extracting a substance to be detected contained in a detection target in an analyte according to claim 4, comprising:
the sample droplet receiving member;
the labeling substance retaining member having a labeling substance containing part; a chromatography medium member having a detection part;
an absorption member;
a nitrous acid compound; and
the acid dianhydride,
wherein the sample droplet receiving member, the labeling substance retaining member, the chromatography medium member and the absorption member are arranged in a manner that a sample develops in the members in this order,
the immunochromatographic device has a part containing the nitrous acid compound and a part containing the acid dianhydride at upstream positions from the detection part, and
the part containing the acid dianhydride is composed of the pad used for the immunochromatographic device for extracting the substance to be detected contained in the detection target in the analyte with nitrous acid.

6. The immunochromatographic device according to claim 5, wherein the nitrous acid compound is a nitrite.

7. An immunochromatographic kit, comprising:
the immunochromatographic device according to claim 4; and
an analyte dilution solution for diluting and developing the analyte.

8. A pad used for an immunochromatographic device for extracting a substance to be detected contained in a detection target in an analyte with nitrous acid, comprising:
an acid anhydride having vapor pressure at 25° C. of $5\times10^{-2}$ Pa or less and solubility in water at 25° C. of 0.1 mg/L or more, wherein the acid anhydride is one or more kinds selected from the group consisting of bicyclo[2,2,2]oct-7-ene-2,3,5,6-tetracarboxylic dianhydride, 1,2,4,5-cyclohexanetetracarboxylic dianhydride, 4-(2,5-dioxotetrahydrofuran-3-yl)-1,2,3,4-tetrahydronaphthalene-1,2-dicarboxylic anhydride, 3-acetamidophthalic anhydride, and 4-(1-propynyl) phthalic anhydride, wherein the pad is impregnated with the acid anhydride, and the pad is in fluid communication with a sample droplet receiving member of the immunochromatographic device, at an upstream position or downstream position from a labeling substance retaining member.

9. The pad according to claim 8, wherein the vapor pressure at 25° C. of the acid anhydride is $2\times10^{-2}$ Pa or less.

10. The pad according to claim 8, wherein a content of the acid anhydride in the pad is 0.4 µmol to 8.4 µmol, per one pad.

11. An immunochromatographic device for extracting a substance to be detected contained in a detection target in an analyte with nitrous acid, comprising the pad according to claim 8.

12. The immunochromatographic device for extracting a substance to be detected contained in a detection target in an analyte according to claim 11, comprising:
the sample droplet receiving member;
the labeling substance retaining member having a labeling substance containing part; a chromatography medium member having a detection part;
an absorption member;
a nitrous acid compound; and
the acid anhydride,
wherein the sample droplet receiving member, the labeling substance retaining member, the chromatography medium member and the absorption member are arranged in a manner that a sample develops in the members in this order,
the immunochromatographic device has a part containing the nitrous acid compound and a part containing the acid anhydride at upstream positions from the detection part, and
the part containing the acid anhydride is composed of the pad used for the immunochromatographic device for extracting the substance to be detected contained in the detection target in the analyte with nitrous acid.

13. The immunochromatographic device according to claim 12, wherein the nitrous acid compound is a nitrite.

14. An immunochromatographic kit, comprising:
the immunochromatographic device according to claim 11; and
an analyte dilution solution for diluting and developing the analyte.

* * * * *